United States Patent [19]
L'Hernault

[11] Patent Number: 6,019,974
[45] Date of Patent: Feb. 1, 2000

[54] SPE-4 PEPTIDES

[75] Inventor: Steven W. L'Hernault, Atlanta, Ga.

[73] Assignee: Emory University, Atlanta, Ga.

[21] Appl. No.: 08/788,231

[22] Filed: Jan. 24, 1997

Related U.S. Application Data

[60] Provisional application No. 60/010,672, Jan. 26, 1996, abandoned.

[51] Int. Cl.[7] .............................. C07K 7/00; A61K 39/00
[52] U.S. Cl. ..................................... 424/191.1; 424/185.1; 424/184.1; 424/192.1; 424/193.1; 424/194.1; 530/300; 530/350; 530/326; 530/327; 530/387.1
[58] Field of Search ..................................... 530/300, 350, 530/326, 327, 387.1; 424/184.1, 185.1, 192.1, 193.1, 194.1, 191.1

[56] References Cited

PUBLICATIONS

Sambrook et al. Molecular Cloning, A Laboratory Manual Second ed. 1989, Chapter 17, 17.2–17.4, 17.8–17.13.
Harlow et al. Antibodies, A Laboratory Manual 1980, Chapter 5, pp. 78–79.
Arduengo et al. Molecular Biology of the Cell Thirty–fourth annual meeting of the American–Society for cell biology, Dec. 10–14, 1994., 5 (Suppl), 1994, 219A, Abstract No. 1275.
Goate et al., (1991) Nature 349:704–706.
L'Hernault et al. (1992) J. Cell Biol. 119:55–68.
Levitan and Greenwald (1995) Nature 377:351–354.
Okamoto and Thomson (1985) J. Neurosci 5:643–653.
Saunders et al. (1993) Neurology 43:1467–1472.
Schellenberg et al. (1992) Science 258:668–671.
Sherrington et al. (1995) Nature 375:754–760.
Strittmatter et al. (1993) Proc. Natl. Acad. Sci. USA 90:1977–1981.

*Primary Examiner*—Anthony C. Caputa
*Assistant Examiner*—Khalid Masood
*Attorney, Agent, or Firm*—Greenlee, Winner and Sullivan, P.C.

[57] ABSTRACT

This application discloses SPE-4 related peptides, peptide-carrier protein conjugates and fusion proteins, immunogenic compositions, antibodies and methods for characterizing the SPE-4 related protein profiles, useful in diagnosing or monitoring SPE-4 related protein profiles of nematodes and/or Alzheimer's disease patients, either in postmortem tissue, preferably from the frontal cortex of the brain, or from other tissue samples, including without limitation muscles and peripheral blood or in a tissue samples of a living patient, where the tissue analyzed can includes brain, muscle or peripheral blood cells.

1 Claim, 1 Drawing Sheet

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
       (A) LENGTH: 2539 base pairs
       (B) TYPE: nucleic acid
       (C) STRANDEDNESS: double
       (D) TOPOLOGY: Not Relevant (ii) MOLECULE TYPE: DNA (genomic)

(iii) HYPOTHETICAL: NO (vi) ORIGINAL SOURCE:
       (A) ORGANISM: Caenorhabditis elegans (vii) IMMEDIATE SOURCE:
       (B) CLONE: SPE4

(ix) FEATURE:
       (A) NAME/KEY: CDS
       (B) LOCATION: join(305..511, 894..1148, 1191..1326,
           1374..1447, 1495..1720, 1792..2049, 2114..2260,
           2310..2401)

(xi) SEQUENCE DESCRIPTION: SEQ ID NO:1:

```
AGCTTAGGAT CCTAGAAGAA GGGTTTTTCG AAACGAATTG GAGTACTGTA GAGTGGTTGT      60

TCTGATCAAG CTCTGAAAGA GAGCATTTCT AGAAAAAAGC ACGACATGTA CAATGCTTGT     120

TCAATTTTTC ACTTCAATGT TAGAAACGGC AATATTCTTC CAAAATAATA TTTTAAAATG     180

ATTTCATCGT GACCCCGTGA TCCAAACCAA AGTACAAACA TGCACGTGTC ATACTTTTGT     240

CTGCCAACTC ATCAATTTCA TACAAATCTC TTGTGCTAAT ATTAATTTTA TTACCTGTCT     300

AAAA ATG GAC ACC CTT CGA TCG ATT TCT AGC GAA TTA GTG CGA TCT TCA      349
     Met Asp Thr Leu Arg Ser Ile Ser Ser Glu Leu Val Arg Ser Ser
      1               5                  10                  15

CAA TTA CGA TGG ACA CTG TTC TCT GTT ATT GCC AAT ATG TCA CTG ACA       397
Gln Leu Arg Trp Thr Leu Phe Ser Val Ile Ala Asn Met Ser Leu Thr
             20                  25                  30

TTG TCT ATT TGG ATT GGA GTT TAC AAC ATG GAA GTG AAT TCT GAA TTG       445
Leu Ser Ile Trp Ile Gly Val Tyr Asn Met Glu Val Asn Ser Glu Leu
         35                  40                  45

AGC AAG ACT TAT TTT TTG GAT CCT TCG TTT GAG CAA ACA ACT GGA AAT       493
Ser Lys Thr Tyr Phe Leu Asp Pro Ser Phe Glu Gln Thr Thr Gly Asn
     50                  55                  60

TTG CTG TTG GAT GGA TTT GTGAGTTTGG ACTGCACATT CTGAGTTTTT              541
Leu Leu Leu Asp Gly Phe
 65

GAGTTAGAGA ATAACATTTT AATTCTTAAT TTACTAGAGT TATTTCTGGG CATGATTCCC     601

CAAATGTTTT GGAGCTTGAT TATTTCGGAT TGATCCTGCA ATTCAAGAAA AGAGACATCC     661

AACATTACAT TTCACAACAA GAAGTTGAAT ACTTTTATCA TTTTAAAAAC CGGCAAGAAA     721

TAGGAAGACA CGTCTTCCGG TGGTCTACCT ACCTACTTGC CTACCTATTT GTCTACGTTT     781

CGCACGAAGC ATAAATTGAA TTTCTTTGTA GTTTATCAAA AAAGTTTGCC ACTCGTACAT     841

TATAATAATT TAATACTCTC TTCCACTTTC AGTTCTCATA TTTTCATTTC AG ATC         896
                                                          Ile
                                                           70

AAT GGA GTT GGT ACA ATT CTC GTT CTT GGA TGC GTC TCT TTC ATA ATG       944
```

```
Asn Gly Val Gly Thr Ile Leu Val Leu Gly Cys Val Ser Phe Ile Met
             75                  80                  85

CTC GCT TTC GTA CTC TTT GAT TTC CGT CGT ATC GTA AAA GCC TGG CTC       992
Leu Ala Phe Val Leu Phe Asp Phe Arg Arg Ile Val Lys Ala Trp Leu
             90                  95                 100

ACA CTT TCA TGT CTT TTG ATA TTG TTT GGG GTA TCC GCG CAG ACT CTT      1040
Thr Leu Ser Cys Leu Leu Ile Leu Phe Gly Val Ser Ala Gln Thr Leu
            105                 110                 115

CAT GAT ATG TTT TCA CAA GTA TTT GAC CAA GAT GAC AAC AAT CAA TAT      1088
His Asp Met Phe Ser Gln Val Phe Asp Gln Asp Asp Asn Asn Gln Tyr
            120                 125                 130

TAC ATG ACA ATT GTG TTG ATA GTG GTT CCA ACG GTT GTA TAT GGG TTC      1136
Tyr Met Thr Ile Val Leu Ile Val Val Pro Thr Val Val Tyr Gly Phe
135                 140                 145                 150

GGA GGG ATC TAT GTAAGTGTTA TGTAACCAAA TAAAAATTAA TAATTATTTA          1188
Gly Gly Ile Tyr

AG GCA TTC TTC TCT AAC AGT TCT TTG ATT CTT CAT CAA ATA TTC GTT       1235
   Ala Phe Phe Ser Asn Ser Ser Leu Ile Leu His Gln Ile Phe Val
       155                 160                 165

GTC ACA AAC TGT TCT CTT ATC TCC GTT TTC TAC CTA CGA GTT TTT CCA      1283
Val Thr Asn Cys Ser Leu Ile Ser Val Phe Tyr Leu Arg Val Phe Pro
170                 175                 180                 185

AGC AAA ACC ACT TGG TTT GTT CTC TGG ATT GTT CTA TTT TGG G            1326
Ser Lys Thr Thr Trp Phe Val Leu Trp Ile Val Leu Phe Trp
                190                 195

GTTTGTTTTC TTCCTGTGCT CTTATGCATT TAATTAAGTT TTTCCAG AT CTC TTT      1381
                                                    Asp Leu Phe
                                                        200

GCC GTT TTA GCA CCG ATG GGT CCA CTC AAA AAA GTT CAA GAA AAG GCT      1429
Ala Val Leu Ala Pro Met Gly Pro Leu Lys Lys Val Gln Glu Lys Ala
            205                 210                 215

TCA GAC TAC AGT AAA TGC GTAAGAATAG CAATTTTCAA AATAAATCTG            1477
Ser Asp Tyr Ser Lys Cys
220

ATTATTTTCA TTTTCAG GTT CTC AAT TTA ATT ATG TTT TCT GCT AAT GAA      1527
                Val Leu Asn Leu Ile Met Phe Ser Ala Asn Glu
                    225                 230                 235

AAA CGT TTA ACT GCA GGA TCC AAT CAA GAA GAG ACA AAT GAA GGA GAG      1575
Lys Arg Leu Thr Ala Gly Ser Asn Gln Glu Glu Thr Asn Glu Gly Glu
                240                 245                 250

GAG AGT ACA ATC AGA AGA ACC GTG AAG CAA ACG ATT GAA TAT TAT ACA      1623
Glu Ser Thr Ile Arg Arg Thr Val Lys Gln Thr Ile Glu Tyr Tyr Thr
            255                 260                 265

AAA CGT GAA GCT CAA GAT GAT GAA TTT TAT CAA AAG ATC AGA CAA CGT      1671
Lys Arg Glu Ala Gln Asp Asp Glu Phe Tyr Gln Lys Ile Arg Gln Arg
            270                 275                 280

CGG GCT GCA ATC AAT CCA GAT TCG GTA CCA ACT GAG CAT AGC CCA TTA G    1720
Arg Ala Ala Ile Asn Pro Asp Ser Val Pro Thr Glu His Ser Pro Leu
285                 290                 295

GTAAGAATTA AATAAATCAT TTAGATCTTT ATAAGAATGA CAGTTGCTAT TATTCATTTT    1780

TTCTTTTTCA G TA GAA GCC GAG CCA TCA CCA ATC GAA TTA AAG GAA AAG      1829
             Val Glu Ala Glu Pro Ser Pro Ile Glu Leu Lys Glu Lys
                 300                 305                 310

AAC AGT ACC GAG GAG CTC AGT GAT GAT GAG AGT GAT ACA TCT GAA ACT      1877
Asn Ser Thr Glu Glu Leu Ser Asp Asp Glu Ser Asp Thr Ser Glu Thr
            315                 320                 325

TCA AGT GGA TCA TCT AAT TTA TCG TCT TCC GAC TCA AGC ACC ACT GTG      1925
Ser Ser Gly Ser Ser Asn Leu Ser Ser Ser Asp Ser Ser Thr Thr Val
            330                 335                 340
```

-continued

```
TCA ACA TCT GAT ATA AGC ACT GCT GAG GAA TGT GAT CAG AAG GAG TGG            1973
Ser Thr Ser Asp Ile Ser Thr Ala Glu Glu Cys Asp Gln Lys Glu Trp
345                 350                 355                 360

GAT GAT TTG GTC TCT AAC AGT CTA CCG AAC AAT GAT AAA CGG CCA GCC            2021
Asp Asp Leu Val Ser Asn Ser Leu Pro Asn Asn Asp Lys Arg Pro Ala
                365                 370                 375

ACT GCT GCG GAC GCC CTT AAT GAT GGA G GTAATAATAG TTTCGTCATA                2069
Thr Ala Ala Asp Ala Leu Asn Asp Gly
            380                 385

TTAAGCTTAC TCTCTTACCA GCTTTTTTTA CGAGAAAGTT TCAG  AA GTA CTT CGT           2124
                                                    Glu Val Leu Arg

CTC GGC TTT GGA GAT TTC GTC TTC TAC AGT CTT CTG ATT GGT CAA GCG            2172
Leu Gly Phe Gly Asp Phe Val Phe Tyr Ser Leu Leu Ile Gly Gln Ala
390                 395                 400                 405

GCT GCC AGC GGA TGT CCA TTT GCA GTC ATT TCT GCC GCT CTT GGT ATT            2220
Ala Ala Ser Gly Cys Pro Phe Ala Val Ile Ser Ala Ala Leu Gly Ile
                410                 415                 420

TTA TTT GGA CTT GTT GTG ACT CTC ACT GTC TTT TCA ACT G                      2260
Leu Phe Gly Leu Val Val Thr Leu Thr Val Phe Ser Thr
                425                 430

GTAATCACCA TATGAATCAC GAAGTTCAAT ACTAATTGTC TCGTTTCAG  AG GAA              2314
                                                         Glu Glu
                                                         435

TCC ACA ACT CCT GCT CTG CCG TTG CCT GTG ATT TGT GGT ACT TTC TGC            2362
Ser Thr Thr Pro Ala Leu Pro Leu Pro Val Ile Cys Gly Thr Phe Cys
        440                 445                 450

TAT TTC AGT TCA ATG TTT TTC TGG GAG CAA CTT TAC GGA TGAAGCCTCA             2411
Tyr Phe Ser Ser Met Phe Phe Trp Glu Gln Leu Tyr Gly
            455                 460                 465

TTTTTCCTGA TATTATGTGA ACTGATTAAA TGTCTTATTT ACTTGTCTGA ATGATTAATT          2471

TTAACCTTTT CGTTTTTTTT TTTAATTTTA TGAATACGAA TCTATTTGGC AAAGAATACA          2531

TAGTATCG                                                                    2539

(2) INFORMATION FOR SEQ ID NO:2:

(i) SEQUENCE CHARACTERISTICS:
        (A) LENGTH: 465 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Thr Leu Arg Ser Ile Ser Ser Glu Leu Val Arg Ser Ser Gln
1               5                   10                  15

Leu Arg Trp Thr Leu Phe Ser Val Ile Ala Asn Met Ser Leu Thr Leu
            20                  25                  30

Ser Ile Trp Ile Gly Val Tyr Asn Met Glu Val Asn Ser Glu Leu Ser
        35                  40                  45

Lys Thr Tyr Phe Leu Asp Pro Ser Phe Glu Gln Thr Thr Gly Asn Leu
    50                  55                  60

Leu Leu Asp Gly Phe Ile Asn Gly Val Gly Thr Ile Leu Val Leu Gly
65                  70                  75                  80

Cys Val Ser Phe Ile Met Leu Ala Phe Val Leu Phe Asp Phe Arg Arg
                85                  90                  95

Ile Val Lys Ala Trp Leu Thr Leu Ser Cys Leu Leu Ile Leu Phe Gly
            100                 105                 110
```

-continued

```
Val Ser Ala Gln Thr Leu His Asp Met Phe Ser Gln Val Phe Asp Gln
        115                 120                 125

Asp Asp Asn Asn Gln Tyr Tyr Met Thr Ile Val Leu Ile Val Val Pro
130                 135                 140

Thr Val Val Tyr Gly Phe Gly Gly Ile Tyr Ala Phe Phe Ser Asn Ser
145                 150                 155                 160

Ser Leu Ile Leu His Gln Ile Phe Val Val Thr Asn Cys Ser Leu Ile
                165                 170                 175

Ser Val Phe Tyr Leu Arg Val Phe Pro Ser Lys Thr Thr Trp Phe Val
                180                 185                 190

Leu Trp Ile Val Leu Phe Trp Asp Leu Phe Ala Val Leu Ala Pro Met
                195                 200                 205

Gly Pro Leu Lys Lys Val Gln Glu Lys Ala Ser Asp Tyr Ser Lys Cys
        210                 215                 220

Val Leu Asn Leu Ile Met Phe Ser Ala Asn Glu Lys Arg Leu Thr Ala
225                 230                 235                 240

Gly Ser Asn Gln Glu Glu Thr Asn Glu Gly Glu Ser Thr Ile Arg
                245                 250                 255

Arg Thr Val Lys Gln Thr Ile Glu Tyr Tyr Thr Lys Arg Glu Ala Gln
                260                 265                 270

Asp Asp Glu Phe Tyr Gln Lys Ile Arg Gln Arg Ala Ala Ile Asn
                275                 280                 285

Pro Asp Ser Val Pro Thr Glu His Ser Pro Leu Val Glu Ala Glu Pro
        290                 295                 300

Ser Pro Ile Glu Leu Lys Glu Lys Asn Ser Thr Glu Glu Leu Ser Asp
305                 310                 315                 320

Asp Glu Ser Asp Thr Ser Glu Thr Ser Ser Gly Ser Ser Asn Leu Ser
                325                 330                 335

Ser Ser Asp Ser Ser Thr Thr Val Ser Thr Ser Asp Ile Ser Thr Ala
                340                 345                 350

Glu Glu Cys Asp Gln Lys Glu Trp Asp Asp Leu Val Ser Asn Ser Leu
                355                 360                 365

Pro Asn Asn Asp Lys Arg Pro Ala Thr Ala Ala Asp Ala Leu Asn Asp
        370                 375                 380

Gly Glu Val Leu Arg Leu Gly Phe Gly Asp Phe Val Phe Tyr Ser Leu
385                 390                 395                 400

Leu Ile Gly Gln Ala Ala Ala Ser Gly Cys Pro Phe Ala Val Ile Ser
                405                 410                 415

Ala Ala Leu Gly Ile Leu Phe Gly Leu Val Val Thr Leu Thr Val Phe
                420                 425                 430

Ser Thr Glu Glu Ser Thr Thr Pro Ala Leu Pro Leu Pro Val Ile Cys
        435                 440                 445

Gly Thr Phe Cys Tyr Phe Ser Ser Met Phe Phe Trp Glu Gln Leu Tyr
        450                 455                 460

Gly
465
```

(2) INFORMATION FOR SEQ ID NO:3:

(i) SEQUENCE CHARACTERISTICS:
        (A) LENGTH: 18 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:3:

```
Cys Leu Arg Leu Gly Phe Asp Phe Val Phe Tyr Ser Leu Leu Ile Gly
1               5                   10                  15

Gln Ala
```

(2) INFORMATION FOR SEQ ID NO:4:

(i) SEQUENCE CHARACTERISTICS:
        (A) LENGTH: 19 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:4:

```
Ile Ser Ala Ala Leu Gly Ile Leu Phe Gly Leu Val Val Thr Leu Thr
1               5                   10                  15

Val Phe Ser
```

(2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:5:

```
Ser Thr Thr Pro Ala Leu Pro Leu Pro Val Ile Cys Gly Thr Phe Cys
1               5                   10                  15
```

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:6:

```
Cys His Asp Met Phe Ser Gln Val Phe Asp Gln Asp Asn Asn Gln
1               5                   10                  15

Tyr
```

(2) INFORMATION FOR SEQ ID NO:7:

(i) SEQUENCE CHARACTERISTICS:
        (A) LENGTH: 21 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:7:

Cys Asp Gln Lys Glu Trp Asp Asp Leu Val Ser Asn Ser Pro Asn Asn
1               5                   10                  15

Asp Lys Arg Pro Ala
            20

(2) INFORMATION FOR SEQ ID NO:8:

(i) SEQUENCE CHARACTERISTICS:
            (A) LENGTH: 20 amino acids
            (B) TYPE: amino acid
            (C) STRANDEDNESS: single
            (D) TOPOLOGY: Not Relevant (ii) MOLECULE TYPE: peptide (iii) HYPOTHETICAL: NO (xi) SEQUENCE DESCRIPTION: SEQ ID NO:8:

Cys Asp Lys Arg Pro Ala Thr Ala Ala Asp Ala Leu Asn Asp Gly Glu
1               5                   10                  15

Val Leu Arg Leu
            20

(2) INFORMATION FOR SEQ ID NO:9:

(i) SEQUENCE CHARACTERISTICS:
            (A) LENGTH: 16 amino acids
            (B) TYPE: amino acid
            (C) STRANDEDNESS: single
            (D) TOPOLOGY: Not Relevant (ii) MOLECULE TYPE: peptide (iii) HYPOTHETICAL: NO (xi) SEQUENCE DESCRIPTION: SEQ ID NO:9:

His Asp Met Phe Ser Gln Val Phe Asp Gln Asp Asp Asn Asn Gln Tyr
1               5                   10                  15

(2) INFORMATION FOR SEQ ID NO:10:

(i) SEQUENCE CHARACTERISTICS:
            (A) LENGTH: 20 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO:10:

Asp Gln Lys Glu Trp Asp Asp Leu Val Ser Asn Ser Pro Asn Asn Asp
1               5                   10                  15

Lys Arg Pro Ala
            20

(2) INFORMATION FOR SEQ ID NO:11:

(i) SEQUENCE CHARACTERISTICS:
            (A) LENGTH: 19 amino acids
            (B) TYPE: amino acid
            (C) STRANDEDNESS: single
            (D) TOPOLOGY: Not Relevant (ii) MOLECULE TYPE: peptide (iii) HYPOTHETICAL: NO (xi) SEQUENCE DESCRIPTION: SEQ ID NO:11:

Asp Lys Arg Pro Ala Thr Ala Ala Asp Ala Leu Asn Asp Gly Glu Val
1               5                   10                  15

Leu Arg Leu (2) INFORMATION FOR SEQ ID NO:12:

(i) SEQUENCE CHARACTERISTICS:
        (A) LENGTH: 17 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:12:

Leu Arg Leu Gly Phe Asp Phe Val Phe Tyr Ser Leu Leu Ile Gly Gln
1               5                   10                  15

Ala (2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:13:

Cys Ile Ser Ala Ala Leu Gly Ile Leu Phe Gly Leu Val Val Thr Leu
1               5                   10                  15

Thr Val Phe Ser
            20

(2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:14:

Cys Ser Thr Thr Pro Ala Leu Pro Leu Pro Val Ile Cys Gly Thr Phe
1               5                   10                  15

Cys (2) INFORMATION FOR SEQ ID NO:15:

(i) SEQUENCE CHARACTERISTICS:
        (A) LENGTH: 20 amino acids
        (B) TYPE: amino acid
        (C) STRANDEDNESS: single
        (D) TOPOLOGY: Not Relevant (ii) MOLECULE TYPE: peptide (iii) HYPOTHETICAL: YES (xi) SEQUENCE DESCRIPTION: SEQ ID NO:15:

```
Lys Lys Glu Pro Gln Glu Ala Leu Phe Ser Val Lys Gln Tyr Phe Tyr
1               5                  10                 15
Thr Val Ala Pro
            20
```

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS: single
        (D) TOPOLOGY: Not Relevant (ii) MOLECULE TYPE: peptide (iii) HYPOTHETICAL: YES (xi) SEQUENCE DESCRIPTION: SEQ ID NO:16:

```
Glu Lys Glu Ser Gln Glu Val Leu Phe Ser Leu Arg Arg Tyr Phe Cys
1               5                  10                 15
Pro Ala Ala Pro
            20
```

(2) INFORMATION FOR SEQ ID NO:17:

(i) SEQUENCE CHARACTERISTICS:
        (A) LENGTH: 465 amino acids
        (B) TYPE: amino acid
        (C) STRANDEDNESS: single
        (D) TOPOLOGY: unknown (ii) MOLECULE TYPE: protein (iii) HYPOTHETICAL: YES (vi) ORIGINAL SOURCE:
        (A) ORGANISM: Homo sapiens (xi) SEQUENCE DESCRIPTION: SEQ ID NO:17:

```
Met Thr Glu Leu Pro Ala Pro Leu Ser Tyr Phe Gln Asn Ala Gln Met
1               5                  10                 15

Ser Glu Asp Asn His Leu Ser Asn Thr Val Arg Ser Gln Asn Asp Asn
                20                  25                 30

Arg Glu Arg Gln Glu His Asn Asp Arg Arg Ser Leu Gly His Pro Glu
            35                  40                 45

Pro Leu Ser Asn Gly Arg Pro Gln Gly Asn Ser Arg Gln Val Val Glu
        50                  55                 60

Gln Asp Glu Glu Glu Asp Glu Glu Leu Thr Leu Lys Tyr Gly Ala Lys
65                  70                  75                 80

His Val Ile Met Leu Phe Val Pro Val Thr Leu Cys Met Val Val Val
                    85                  90                 95

Val Ala Thr Ile Lys Ser Val Ser Phe Tyr Thr Arg Lys Asp Gly Gln
                100                 105                110

Leu Ile Tyr Thr Pro Phe Thr Glu Asp Thr Glu Thr Val Gly Gln Arg
                115                 120                125

Ala Leu His Ser Ile Leu Asn Ala Ala Ile Met Ile Ser Val Ile Val
            130                 135                 140

Val Met Thr Ile Leu Leu Val Val Leu Tyr Lys Tyr Arg Cys Tyr Lys
145                 150                 155                160
```

-continued

Val Ile His Ala Trp Leu Ile Ile Ser Ser Leu Leu Leu Phe Phe
                165                 170                 175

Phe Ser Phe Ile Tyr Leu Gly Glu Val Phe Lys Thr Tyr Asn Val Ala
                180                 185                 190

Val Asp Tyr Ile Thr Val Ala Leu Leu Ile Trp Asn Phe Gly Val Val
                195                 200                 205

Gly Met Ile Ser Ile His Trp Lys Gly Pro Leu Arg Leu Ala Tyr Leu
    210                 215                 220

Ile Met Ile Ser Ala Leu Met Ala Leu Val Phe Ile Lys Tyr Leu Pro
225                 230                 235                 240

Glu Trp Thr Ala Trp Leu Ile Leu Ala Val Ile Ser Val Tyr Asp Leu
                245                 250                 255

Val Ala Val Leu Cys Pro Lys Gly Pro Leu Arg Met Leu Val Glu Thr
                260                 265                 270

Ala Gln Glu Arg Asn Glu Thr Leu Phe Pro Ala Leu Ile Tyr Ser Ser
                275                 280                 285

Thr Met Val Trp Leu Val Asn Met Ala Glu Gly Asp Pro Glu Ala Gln
    290                 295                 300

Arg Arg Val Ser Lys Asn Ser Lys Tyr Asn Ala Glu Ser Thr Glu Arg
305                 310                 315                 320

Glu Ser Gln Asp Thr Val Ala Glu Asn Asp Asp Gly Gly Phe Ser Glu
                325                 330                 335

Glu Trp Glu Ala Gln Arg Asp Ser His Leu Gly Pro His Arg Ser Thr
                340                 345                 350

Pro Glu Ser Arg Ala Ala Val Gln Glu Leu Ser Ser Ser Ile Leu Ala
                355                 360                 365

Gly Glu Asp Pro Glu Glu Arg Gly Val Lys Leu Gly Leu Gly Asp Phe
    370                 375                 380

Ile Phe Tyr Ser Val Leu Val Gly Lys Ala Ser Ala Thr Ala Ser Gly
385                 390                 395                 400

Asp Trp Asn Thr Thr Ile Ala Cys Phe Val Ala Ile Leu Ile Gly Leu
                405                 410                 415

Cys Leu Thr Leu Leu Leu Leu Ala Ile Phe Lys Lys Ala Leu Pro Ala
                420                 425                 430

Leu Pro Ile Ser Ile Thr Phe Gly Leu Val Phe Tyr Phe Ala Thr Asp
                435                 440                 445

Tyr Leu Val Gln Pro Phe Met Asp Gln Leu Ala Phe His Gln Phe Tyr
    450                 455                 460

Ile
465

(2) INFORMATION FOR SEQ ID NO:18:

(i) SEQUENCE CHARACTERISTICS:
        (A) LENGTH: 465 amino acids
        (B) TYPE: amino acid
        (C) STRANDEDNESS: single
        (D) TOPOLOGY: unknown (ii) MOLECULE TYPE: protein (iii) HYPOTHETICAL: YES (vi) ORIGINAL SOURCE:
        (A) ORGANISM: mouse (xi) SEQUENCE DESCRIPTION: SEQ ID NO:18:

Met Thr Glu Ile Pro Ala Pro Leu Ser Tyr Phe Gln Asn Ala Gln Met

-continued

```
1               5                   10                  15
Ser Glu Asp Ser His Ser Ser Ala Ile Arg Ser Gln Asn Asp Ser
                20              25              30
Gln Glu Arg Gln Gln His Asp Arg Gln Arg Leu Asp Asn Pro Glu
            35              40              45
Pro Ile Ser Asn Gly Arg Pro Gln Ser Asn Ser Arg Gln Val Val Glu
        50              55              60
Gln Asp Glu Glu Asp Glu Glu Leu Thr Leu Lys Tyr Gly Ala Lys
65              70              75              80
His Val Ile Met Leu Phe Val Pro Val Thr Leu Cys Met Val Val
                85              90              95
Val Ala Thr Ile Lys Ser Val Ser Phe Tyr Thr Arg Lys Asp Gly Gln
            100             105             110
Leu Ile Tyr Thr Pro Phe Thr Glu Asp Thr Glu Thr Val Gly Gln Arg
            115             120             125
Ala Leu His Ser Ile Leu Asn Ala Ala Ile Met Ile Ser Val Ile Val
            130             135             140
Ile Met Thr Ile Leu Leu Val Val Leu Tyr Lys Tyr Arg Cys Tyr Lys
145             150             155             160
Val Ile His Ala Trp Leu Ile Ile Ser Ser Leu Leu Leu Phe Phe
                165             170             175
Phe Ser Phe Ile Tyr Leu Gly Glu Val Phe Lys Thr Tyr Asn Val Ala
            180             185             190
Val Asp Tyr Val Thr Val Ala Leu Leu Ile Trp Asn Phe Gly Val Val
            195             200             205
Gly Met Ile Ala Ile His Trp Lys Gly Pro Leu Arg Leu Ala Tyr Leu
210             215             220
Ile Met Ile Ser Ala Leu Met Ala Leu Val Phe Ile Lys Tyr Leu Pro
225             230             235             240
Glu Trp Thr Ala Trp Leu Ile Leu Ala Val Ile Ser Val Tyr Asp Leu
            245             250             255
Val Ala Val Leu Cys Pro Lys Gly Pro Leu Arg Met Leu Val Glu Thr
            260             265             270
Ala Gln Glu Arg Asn Glu Thr Leu Phe Pro Ala Leu Ile Tyr Ser Ser
            275             280             285
Thr Met Val Trp Leu Val Asn Met Ala Glu Gly Asp Pro Glu Ala Gln
290             295             300
Arg Arg Val Pro Lys Asn Pro Lys Tyr Asn Thr Gln Arg Ala Glu Arg
305             310             315             320
Glu Thr Gln Asp Ser Gly Ser Gly Asn Asp Asp Gly Gly Phe Ser Glu
            325             330             335
Glu Trp Glu Ala Gln Arg Asp Ser His Leu Gly Pro His Arg Ser Thr
            340             345             350
Pro Glu Ser Arg Ala Ala Val Gln Glu Leu Ser Gly Ser Ile Leu Thr
            355             360             365
Ser Glu Asp Pro Glu Glu Arg Gly Val Lys Leu Gly Leu Gly Asp Phe
            370             375             380
Ile Phe Tyr Ser Val Leu Val Gly Lys Ala Ser Ala Thr Ala Ser Gly
385             390             395             400
Asp Trp Asn Thr Thr Ile Ala Cys Phe Val Ala Ile Leu Ile Gly Leu
                405             410             415
Cys Leu Thr Leu Leu Leu Leu Ala Ile Phe Lys Lys Ala Leu Pro Ala
            420             425             430
```

```
Leu Pro Ile Ser Ile Thr Phe Gly Leu Val Phe Tyr Phe Ala Thr Asp
    435                 440                 445

Tyr Leu Val Gln Pro Phe Met Asp Gln Leu Ala Phe His Gln Phe Tyr
    450                 455                 460

Ile
465

(2) INFORMATION FOR SEQ ID NO:19:

(i) SEQUENCE CHARACTERISTICS:
        (A) LENGTH: 28 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO:19:

Gln Val Val Leu Asn Ser Ile Ile Lys Ala Met Val Pro Leu Leu His
1               5                   10                  15

Ile Ala Leu Leu Val Leu Phe Val Ile Ile Tyr
            20                  25

(2) INFORMATION FOR SEQ ID NO:20:

(i) SEQUENCE CHARACTERISTICS:
        (A) LENGTH: 16 amino acids
        (B) TYPE: amino acid
        (C) STRANDEDNESS: single
        (D) TOPOLOGY: Not Relevant (ii) MOLECULE TYPE: peptide (iii) HYPOTHETICAL: YES (xi) SEQUENCE DESCRIPTION: SEQ ID NO:20:

Ser Ile Ala Ser Leu Leu Leu Leu Phe Leu Phe Ile Ile Ile Phe
1               5                   10                  15

(2) INFORMATION FOR SEQ ID NO:21:

(i) SEQUENCE CHARACTERISTICS:
        (A) LENGTH: 27 amino acids
        (B) TYPE: amino acid
        (C) STRANDEDNESS: single
        (D) TOPOLOGY: Not Relevant (ii) MOLECULE TYPE: peptide (iii) HYPOTHETICAL: YES (xi) SEQUENCE DESCRIPTION: SEQ ID NO:21:

Val Leu Ser Ala Met Met Ala Leu Phe Thr Val Ser Thr Phe Glu Gly
1               5                   10                  15

Trp Pro Ala Leu Leu Tyr Lys Ala Ile Asp Ser
            20                  25
```

SPE-4 PEPTIDES

CROSS REFERENCE TO RELATED APPLICATIONS

This application claims priority under 35 U.S.C. 119(e) from U.S. Provisional Patent Application Ser. No. 60/010,672, filed Jan. 26, 1996, now abandoned.

ACKNOWLEDGEMENT OF GOVERNMENT FUNDING

This invention was made, at least in part, with funding from the National Institutes of Health (NIH Grant GM 40697 (R01). Accordingly, the United States Government may have certain rights in this invention.

TECHNICAL FIELD OF THE INVENTION

The field of this invention is the area of peptide antigens, antibodies, methods and kits therefor, specifically using antibody preparations raised in response to antigen(s) derived wholly or in part from one or more proteins of the nematode *Caenorhabditis elegans*.

BACKGROUND OF THE INVENTION

Alzheimer's disease (AD) is a significant health problem, and an economic problem as well, in modern society. It is a degenerative disease of the central nervous system; clinical symptoms include progressive memory loss and decline in cognitive functions. Typically, the onset of AD is in the middle to late stages of human life. Late onset AD occurs at ages greater than 60 years while the symptoms of early onset AD appear in affected individuals between 30 and 60 years of age. At the histological level, Alzheimer's disease is characterized by such pathological features as amyloid plaques and intraneuronal neurofibrillary tangles [Sherrington et al. (1995) *Nature* 375:754–760].

Several genetic loci have been implicated in AD, which appears to be complex with respect to its etiology. The 112Cys to Arg allele of ApolE (Apolipoprotein E) is associated with a significant proportion of the late onset AD cases [Strittmatter et al. (1993) *Proc. Natl. Acad. Sci. USA* 90:1977–1981; Saunders et al. (1993) *Neurology* 43:1467–1472]. Mutations in the β-amyloid precursor protein gene (βAPP) have been associated in certain families (<3%) with AD onset prior to 65 years of age [See, e.g., Goate et al. (1991) *Nature* 349:704–706]. A third locus associated with AD is the stm-2 locus on chromosome 1; this gene determines the presenilin protein. Another locus (AD3 on chromosome 14q24.3), which functions as an autosomal dominant locus, may account for up to 70% of the cases of early onset AD [Schellenberg et al. (1992) *Science* 258:1445–1453]. Sherrington et al. (1995) supra has described five different missense mutations in a novel gene called s182, which mutations are associated with early onset AD. Pedigree studies suggested that these mutations confer an autosomal dominant AD phenotype. Sequence analysis of the deduced amino acid sequence indicates that the protein product of this gene is likely to be an integral membrane protein despite the absence of an obvious signal peptide sequence and a dearth of potential glycosylation sites. The human S182 protein shares significant amino acid homology with the *Caenorhabditis elegans* spe-4 gene product, which has been shown to function in spermatogenesis in the nematode [L'Hernault et al. (1992) *J. Cell Biol.* 119:55–69].

To date, conclusive diagnosis has generally required histological analysis of brain tissue, after death. In view of the invasiveness of sampling of brain tissue and the desirability of conclusively diagnosing human disease during life, there is a long felt need in the art for a noninvasive diagnostic test for Alzheimer's disease.

Figure 1:
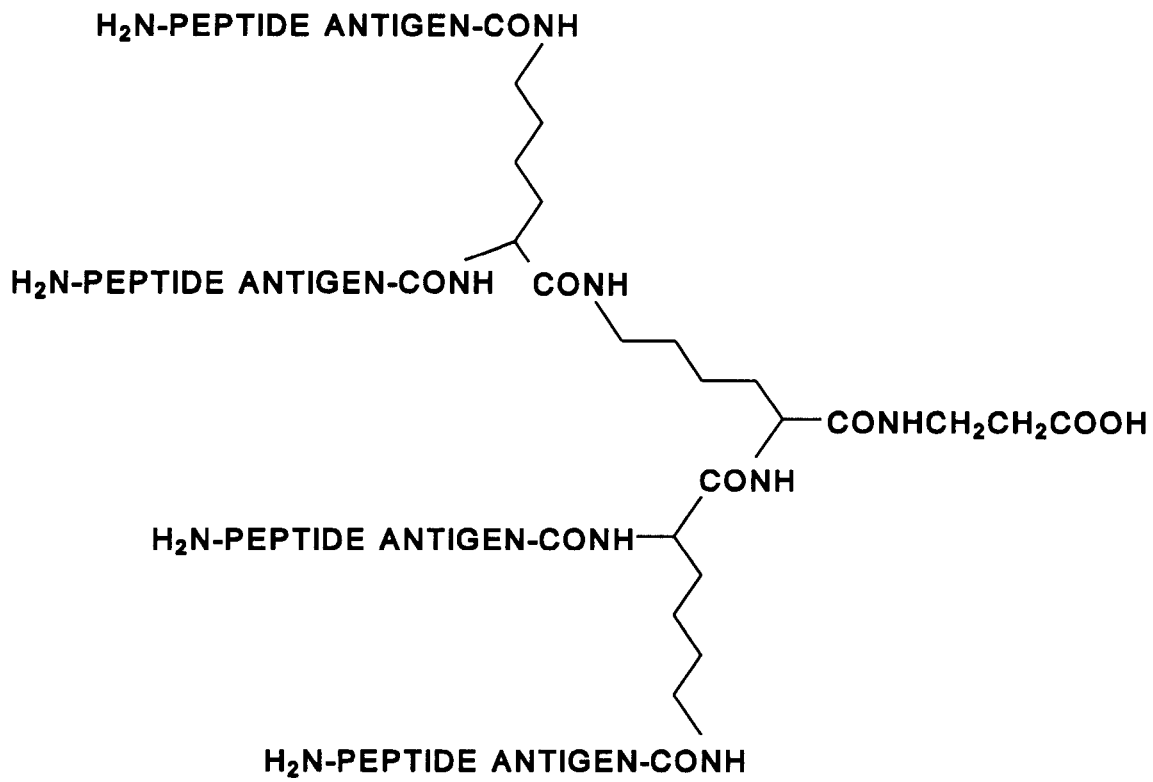
FIG. 1 is a schematic representation of multiple antigen peptide structure.

The peptide branches are each identical in sequence and synthesized simultaneously. Example 1 provides "peptide" sequences assembled on the lysine framework in this study.

SUMMARY OF THE INVENTION

The present invention provides peptides, multiple antigen peptides, peptide-carrier protein conjugates and fusion proteins derived from or related to the *C. elegans* SPE-4 protein. Peptide antigens specifically exemplified herein and useful for the purposes set forth herein include those having amino acid sequences corresponding to amino acids 118–133, 119–134, 354–376, 355–376, 372–389, 372–390, 415–433 and 437–452 each as in SPE-4' (Table 1 and SEQ ID NO:2) hereinbelow). Additional peptides include CLRLGFGDFVFYSLLIGQA, (SEQ ID NO:3); ISAAL-GILFGLVVTLTVFS (SEQ ID NO:4); and STTPAL-PLPVICGTFC. Within the scope of the present invention are peptides of the exemplified sequence conjugated to a carrier (including, but not limited to, bovine serum albumin and keyhole limpet hemocyanin) and/or synthesized as a "multiple antigen peptide." Where peptides are to be coupled to a carrier, a cysteine residue is incorporated at the N-terminus of the peptide having a particular sequence of interest. These SPE-4 related peptides, peptide-protein conjugates and fusion proteins are useful in the preparation of immunogenic compositions for making monoclonal and/or polyclonal antibody preparations. Such antibody preparations comprising antibodies specific for said peptides, conjugates and fusion proteins are useful in screening and characterizing the protein products of the *C. elegans* spe-4 and sel-12 genes and the human S182 and STM-2 presenilin proteins and variants thereof, for example, by Western (immuno)blotting.

Variants of said human proteins are characteristic of Alzheimer's Disease patient tissue. Protein profiles can be characterized using brain tissue, either from autopsy or biopsy, and protein profiles can also be characterized using peripheral blood cells and\or muscle tissue, among others.

Antibody preparations comprising antibodies made in response to and specific to peptides referred to above and as set forth hereinbelow and fusion proteins described herein (see Examples 1–2) useful in the characterization of SPE-4 related protein profiles of normal individuals and Alzheimer's Disease patients can include those antisera prepared using immunogens including those with an amino acid sequence as given in Table 1: amino acids 118–133, amino acids 354–376 and amino acids 372–389, each of which is from the SPE-4 protein's primary structure. Other similarly useful peptides include those with cysteine residues at the amino ends and those consensus sequence-based peptides disclosed herein.

DETAILED DESCRIPTION OF THE INVENTION

*Caenorhabditis elegans* is a nematode which has been extensively characterized with respect to numerous aspects of its developmental and molecular biology. Disruption in the *C. elegans* spe-4 gene results in a male-sterile phenotype. Ultrastructural studies revealed that spe-4 mutant spermatocytes exhibited disruption of the membrane rich organelles called the fibrous body-membranous organelle complexes (FB-MO complexes) [L'Hernault and Arduengo (1992) *J. Cell. Biol.* 119:55–68]. A nearly full-length cDNA has been cloned and sequenced (See Table 1 for the genomic nucleotide sequence and the deduced amino acid sequence). The protein product of the spe-4 gene is the SPE-4 protein, which is an integral membrane protein. The spe-4 cDNA and genomic sequences are available from EMBL/Genbank/DDBJ as accession numbers Z14066 and Z14067, respectively.

SPE-4 related proteins and peptides are those which cross-react with antibodies directed against the peptides disclosed herein which have sequences derived from the SPE-4 amino acid sequence or which have sequences derived from consensus sequences generated from comparisons of SPE-4 and S182 and/or comparisons of SPE-4, S182 and SEL-12.

Table 1 presents 2539 nucleotides of genomic sequence. The transcription start site, numbered "1", was determined in primer extension experiments. The translation start site (ATG) begins at nucleotide 16 and the termination codon for the spe-4 open reading frame ends at nucleotide 1413, Table 1. See also SEQ ID NOS:1–2. The cDNA sequence appears in upper case, non-italicized letters; introns and flanking regions appear in lower case letters. The positive numbers at the right side are nucleotide numbers from the sequence of the cDNA pMA7 (See L'Hernault and Arduengo (1992) supra) and primer extension; the 23 nucleotides at the 5' end are upper case and italicized to reflect that they were determined by primer extension of either him-5 males or 25° C. grown fem-3 RNA. The nucleotides in the genomic sequence that are 5' to the 5' end of the primer extension product are negatively numbered and in lower case; and nucleotides within introns and in the 3' flanking regions are in lower case and are not numbered. Italicized numbers at the right of the table refer to amino acid residues. A potential TATA box and CAAT sequences at the 5' end of the gene and a potential polyadenylation signal sequence at the 3' end of the gene are all underlined. The 178 nucleotides of sequence, and the corresponding amino acid residues deleted in the spe-4(q437) mutation appear in bold type. These sequence data are available from EMBL/GenBank/DDBJ under accession no. Z14066 and accession no. Z14067 for the cDNA and genomic sequences, respectively.

Antibodies were produced with the goal of characterizing sperm-specific proteins (SPE-4) and the temporal and spatial control of their synthesis. A nearly full-length SPE-4 cDNA clone was isolated (pMA7). The partial cDNA coding sequence was cloned downstream of an inducible *Escherichia coli* promoter in an expression vector. This construct appeared to be toxic to the bacterial cells. A pMA7 BamHI to BclI fragment was subcloned into the prokaryotic expression vector pGEX-2T [Smith and Johnson (1988) *Gene* 67:31–40] and into pET5a [Studier et al. (1990) *Meth. Enzymol.* 185:60–89]. The resulting expression products are fusion proteins having the *Schistosoma japonicum* glutathione S-transferase (GST, for pGEX-2T) or 11 amino acids of the T7 major capsid protein 10 (for pET5a) at the N-terminus fused to the inserted protein at the C-terminus, in the present context a portion of the spe-4 encoded protein). The hydrophilic spe-4/pGEX-2T construct is termed pOA5 and the spe-4/pET5a construct is call pOA6; each of these constructs contains the spe-4 amino acids starting with a glycine at amino acid 241 and extending to a cysteine residue at amino acid 354 of SPE-4 (Table 1). This portion of the SPE-4 protein has the sequence characteristics of a large hydrophilic loop region.

The pOA6 clone does not appear to induce recombinant protein synthesis very well. However, the pOA5 clone has been successfully used to generate relatively large amounts of the fusion protein. This GST/SPE-4 fusion protein has been used as an immunogen for producing polyclonal antibodies in rabbits. Testing of the antibody preparations indicated that the antisera was largely directed to the spe-4 encoded portions of the antigen because there was no immunological cross reactivity to GST or to the T7 gene capsid 10 protein. Initial results suggested that a nematode protein of about 80 kDa was reactive with the antisera. Surprisingly, there were variable results with these antibody preparations on Western blots containing *C. elegans* proteins. The data from the analysis of RNA populations of the nematode indicated that only animals engaged in spermatogenesis exhibited transcriptional expression of the spe-4 gene. Thus, it had been expected that the antisera would react only with proteins from animals engaged in spermatogenesis.

Because SPE-4 is a seven-pass integral membrane protein as predicted from analysis of the deduced amino acid sequence, experiments were performed to determine if this protein forms a voltage-gated ion channel. Full-length cDNA encoding SPE-4 was microinjected into *Xenopus laevis* oocytes. The experiments were inconclusive with respect to the potential role of SPE-4 in forming ion channels, but it was determined that the membranes of injected oocytes contained a protein of 48 kDa which was not present in the uninjected oocyte control membrane preparations.

Fusion proteins comprising a portion of the glutathione S-transferase (GST) contained within the expression vector pGEX-2T and the large hydrophilic loop region of SPE-4 (amino acids 241 to 354 of SPE-4, see Table 1, see also SEQ ID NO:2) were used as immunogens in rabbits. Fusion protein comprising the N-terminal region of T7 gene 10 capsid protein and the same region of SPE-4 were also made, but this fusion preparation was not used to immunize animals because protein production from the recombinant pET5a clone was poor. There was no cross reactivity either with the intact GST or capsid proteins; thus, the antisera were specific for the SPE-4 portions of the fusion protein used for immunization. Four antibody preparations were used in various experiments disclosed herein: EU20 and EU21 were prepared at Spring Valley Laboratories, Inc. (Woodbine, Md.) and 9910 and 9911 were produced at the Pocono Rabbit Farm and Laboratory (Canadensis, Pa.). All four antisera reacted strongly with the pGEX-2T and pET5a fusion proteins on Western blots.

Immunocytochemical localization experiments were performed using the antisera prepared in response to the fusion proteins, with some unexpected results. As expected all four antisera reacted with *C. elegans* sperm. Surprisingly, these antibody preparations also reacted with sperm from spe-4 null mutant nematodes, which were not expected to contain SPE-4 polypeptide products. Mutant strains which unexpectedly reacted with the antisera included the spe-4(q347) arrested spermatocytes; the spe-4 (q347) mutation is a deletion mutation which results in premature protein chain termination prior to the hydrophilic loop portion of the SPE-4 molecule expressed in the fusion protein of the immunogen. Accordingly, arrested spermatocytes with the spe- 4 (q347) mutation are not expected to express a polypeptide which would cross react with the antisera.

Affinity purification of all four antisera preparations resulted in two outcomes. For antisera 9910 and 9911, the purified antibodies no longer reacted with the spe-4(q347) arrested spermatocytes and staining of wild-type tissue is restricted to spermatids. By contrast, the EU20 and EU21 preparations still reacted strongly with the spe-4 (q347) arrested spermatocytes after affinity purification. The EU20 preparation reacted on Western blots with a protein of about 80 kDa from sperm, but the EU21 preparation did not. both EU20 and EU21 preparations reacted with the pET fusion protein product. All four antibodies reacted strongly and specifically to the FB-MO complexes in wild-type (normal) sperm and spermatocytes. Identity of the FB-MO complexes at the level of light microscopy was confirmed by co-localization with monoclonal antibody 1CB4. Within sperm 1CB4 specifically decorates FB-MO complexes in sperm. This antibody also labels several neurons and intestinal cells when labeled with immunogold and reacted in ultrathin tissue sections and examined by electron microscopy [Okamoto and Thomson (1985) *J. Neurosci.* 5:643–653]. It was a surprising result that the EU20 and EU21 antisera reacted with the disrupted FB-MO complex of the spe-4 (q347) mutant arrested spermatocytes and spe-4 (nc8l) mutant spermatocytes. The antisera were affinity purified to remove potentially extraneous antibodies prior to use in the experiments described herein.

The 11770 preparation has not been affinity purified, but it cross reacts with many protein bands from nematodes on Western blots, including protein bands of about 38 kDa and 48 kDa.

The EU39, EU40 and EU41 preparations have not yet been fully characterized. The EU43 preparation has not been affinity purified or fully characterized, but weak cross reactivity has been observed with a very large protein from male nematodes. The 11950, 11951 and 11952 preparations have not been fully characterized, and the 11950 preparation reacts with prominent protein bands of over 83 and over 140 kDa from nematodes when examined on Western blots.

Because nematode sperm are difficult to purify in relatively large quantities, attempts were made to optimize the Western blotting protocol so that experiments could be performed on whole worm samples. However, Western blot results with the affinity-purified antisera were weak and generally inconclusive. Further studies were carried out with whole sera. One Western blot was obtained in which a 42–44 kDa polypeptide was shown to be present in N2 normal male worms but missing in spe-4 (q347) males. The spe-4 (hc8l) mutant, which is presumed to be a missense mutant, was tested and shown to contain an immunoreactive 42–44 kDa protein as well as a reactive polypeptide of 48 kDa. In addition the wild-type and the two mutant worm samples contained reactive polypeptides of about 25 kDa and about 28 kDa. Other Western blotting experiments with the antisera indicated that the antisera was not specific for proteins only from male worms and that there was immunological cross reactivity with samples from nematodes which did not contain sperm. However, it is noted that membrane proteins are notorious for yielding ambiguous results in Western blotting experiments.

In view of the perceived inconsistencies described above, antisera were generated using peptide antigens derived from portions of the SPE-4 protein other than the hydrophilic loop used in the fusion protein experiments. The peptide sequences were selected based on hydrophilicity so that they would be expected to be good immunogens and soluble for ease in coupling to the carrier proteins used in the immunogenic compositions. Peptides were synthesized to contain amino acid sequences as given in SPE-4 from amino acids 118 to 133 (Peptide 1), from amino acids 354 to 376 (Peptide 2), and from amino acids 372 to 389 (Peptide 3), all with reference to Table 1, SEQ ID NO:2. A cysteine residue was added to the N-termini of Peptides 1 and 3 to allow chemical coupling to the carrier proteins. Each peptide was coupled to bovine serum albumin (BSA) and also to keyhole limpet hemocyanin (KLH) in individual reactions. Rabbits were immunized and antisera were prepared. A summary of the identification numbers and immunogen is as follows: KLH-coupled Peptide 1 was the immunogen for EU11770, 11771 and 11772 prepared at Pocono Rabbit Farm & Laboratory and Peptide 1 coupled to BSA was the immunogen for EU39, EU40 and EU41 from Spring Hill.

Additional SPE-4-related antigen preparations were made using multiple peptide antigen (MAP) technology, in which multiple peptides are synthesized on a base consisting of a plurality of lysine moieties [see, e.g. Tam, J. P. (1988) *Proc. Natl. Acad. Sci. USA* 85:5409–5413; Posnett et al. (1988) *J. Biol. Chem.* 263:1719–1725]. MAP-peptides have the advantage over oligopeptides in that conjugation to a carrier protein is not necessary for use in immunization protocols; additionally, Posnett et al. (1988) supra report that the multi-lysine base does not itself appear to induce a significant antibody response.

Antisera EU41 and 11772 react with a single band of about 50–55 kDa on Western blots in him-5 males, fem-3 (q23) female body, male germline and fem-1 (hc17) females [See chapter by Hodgkin, J. in *The Nematode Caenorhabditis elegans*, W. Wood (ed), 1993, Cold Spring Harbor Laboratory Press, Cold Spring Harbor, N.Y., for a review of sex determination in *C. elegans*]. Thus, the SPE-4 peptide antisera are not sex-specific with respect to the nematode. All unimmunized rabbits tested at this point exhibit background reactivity so antiserum preparations have not been prepared.

Recently, Levitan and Greenwald published the sequence of the somatic analog of spe-4, the sel-12 gene and the SEL-12 protein encoded thereby. The SEL-12 protein shares significant amino acid sequence identity and similarity with the SPE-4 protein and the human S182 protein [Levitan and Greenwald (1995) *Nature* 377:351–354]. Sherrington et al. (1995) supra have described the human s182 gene and its encoded protein S182. Sherrington et al. provided evidence that the S182 protein is synthesized in a variety of human tissues, including brain membranes, and this group also demonstrated reproducible differences in the S182 proteins of the brain tissue of early onset AD victims.

A comparison of the SPE-4, S182, SEL-12 and TO3796 amino acid sequences is presented in Table 2. This comparison was generated using PILEUP software (GCG-Wisconsin package, Madison, Wis.). Peptides having an amino acid sequence as given in one or more of Peptide 1, Peptide 2, Peptide 3, MAP-OP4, MAPSpe4-4, MAPSpe4-5 and MAPSpe4-6, as defined herein, are useful in the generation of antibodies for use in the methods disclosed herein, e.g., for screening nematode and/or human proteins sharing immunological cross reactivity to one or more epitope(s) presented within this peptide.

Without wishing to be bound by any particular theory, it is postulated that human candidate proteins and variants which cross-react with the antibodies specific for the peptide antigens disclosed herein include the gene protein of the early onset AD gene s182, the gene product of the transcript corresponding to the partial cDNA transcript TO3796 recovered from infant human brains and human homologs of the C. elegans genes including sel-12 and spe-4. Variations in the cross-reactive human protein profiles of tissue of normal versus AD patients allows the detection and/or monitoring of AD using noninvasive testing.

In another embodiment, polyclonal and/or monoclonal antibodies capable of specifically binding to a particular AD characteristic protein or fragments thereof are provided. The term antibody is used to refer both to a homogenous molecular entity and a mixture such as a serum product made up of a plurality of different molecular entities. Monoclonal or polyclonal antibodies, preferably monoclonal, specifically reacting with the SPE-4 protein or a peptide derived therefrom or having an amino acid sequence cross-reactive with the SPE-4 protein and human proteins having antigenic cross-reactivity may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1987) supra. Also, recombinant immunoglobulins may be produced by methods known in the art, including but not limited to the methods described in U.S. Pat. No. 4,816,567, incorporated by reference herein. Monoclonal antibodies with affinities of $10^8$ $M^{-1}$, preferably $10^9$ to $10^{10}$ or more are preferred for the methods disclosed herein.

Antibodies generated against the SPE-4 protein or a peptide derived therefrom or having an amino acid sequence cross-reactive with the SPE-4 protein and human proteins having antigenic cross-reactivity and having a characteristic pattern associated with AD are useful, for example, as probes for screening patient tissue or peripheral blood samples for AD-specific protein patterns. These antibodies can be used in tests of samples from living patients or in tests of post mortem tissue or blood samples. Hydrophilic regions of the SPE-4 protein or its human counterpart(s) can be identified by the skilled artisan, and peptide antigens can be synthesized and conjugated to a suitable carrier protein (e.g., bovine serum albumin or keyhole limpet hemocyanin) for use in vaccines. Frequently, the polypeptides and antibodies will be labeled by joining, either covalently or noncovalently, a substance which provides a detectable signal which is useful in diagnostic or other assays of biological material, particularly after resolution of the proteins by polyacrylamide gel electrophoresis, preferably sodium dodecyl polyacrylamide gel electrophoresis. Suitable labels include, but are not limited to, radionuclides, enzymes, substrates, cofactors, inhibitors, fluorescent agents, chemiluminescent agents, magnetic particles and the like. United States patents describing the use of such labels include but are not limited to U.S. Pat. Nos. 3,817,837; 3,850,752; 3,939,350; 3,996,345; 4,277,437; 4,275,149; and 4,366,241.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology; Glover* (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein. All references cited in the present application are incorporated by reference in their entirety herein.

The foregoing discussion and the following examples are provided for illustrative purposes, and they are not intended to limit the scope of the invention as claimed herein. Modifications and variations which may occur to one of ordinary skill in the art are within the intended scope of this invention.

EXAMPLES

Example 1

Peptide Synthesis

Peptides 1–3 were synthesized using standard techniques on an Applied Biosystems Model 433A Peptide Synthesizer (Foster City, Calif.).

Peptide 1 corresponds to amino acids 119–134 of SEQ ID NO:2 plus an (added) N-terminal cysteine to allow coupling to carrier proteins. Peptide 2 has the amino acid sequence of amino acids 355–376 of SPE-4. Peptide 3 corresponds to amino acids 372–390 of SPE-4, plus an (added) N-terminal cysteine to allow conjugation to carrier proteins. MAP-peptide SPE-4 has the amino acid sequence of residues 372–390 of SPE-4 with an (added) N-terminal cysteine residue. MAP SPE4-5 corresponds in sequence to amino acids 415–433 of SPE-4. MAP SPE4-6 has the sequence of amino acids 437–452 of the SPE-4 protein. The "MAP" peptides are each synthesized on a lysine backbone; the schematic structure is shown in FIG. 1. The genomic nucleotide sequence encoding C. elegans SPE-4 and its deduced amino acid sequence are given in Table 1. See also SEQ ID NOS:1–2 Oligopeptides (CLRLGF) were assembled on this machine.

Multiple Antigen Peptides were synthesized using the Fmoc/t-butyl strategy on a multiple antigen peptide (MAP) tetra-branched Wang resin (substitution 0.42 mmol/g, Advanced Chem Tech, Louisville, Ky.). Three peptides, MAP-OP4, MAPSpe4-5 and MAPSpe4-6, were assembled on the Rainin Instruments Model Symphony/Multiplex multiple peptide synthesizer (Woburn, Mass.). The sequence of the peptide assembled onto the MAP-OP4 is CLRLGFGDFVFYSLLIGQA, (SEQ ID NO:3) the peptide portion of Spe4-5 is ISAALGILFGLVVTLTVFS, (SEQ ID NO:4) and the peptide portion of Spe4-6 is STTPALPLPVICGTFC, SEQ ID NO:5. The Spe4-5 MAP is insoluble in common solvents, and must be used in suspension rather than in solution. The general structure of a MAP peptide is shown in FIG. 1.

After synthesis the peptides were cleaved from the resin and side chain deprotected using trifluoroacetic acid (TFA) :p-cresol:phenol:ethane dithiol:water (82.5:5:5:2.5:5, v/v). Following cleavage, the peptides were precipitated with cold diethyl ether, centrifuged and the peptide precipitate was washed twice with cold ether.

The Spe4-6 peptide was lyophilized and the crude peptide was supplied as a TFA salt. The SEQ ID NO:3 peptide was suspended in dilute aqueous acetic acid, dialyzed for 48 hrs against HPLC grade water and lyophilized, yielding an acetate salt of the crude peptide. Spe4-5 was purified by reverse phase HPLC on a C8 silica Vydac (Hesperia, Calif.) preparative column (2.5×25 cm); the peptide was eluted using a linear gradient of acetonitrile in 0.1w aqueous TFA. The purified peptide was lyophilized and supplied as a TFA salt.

The purity and structural integrity of each peptide was confirmed by quantitative amino acid analysis, mass spectrometry and N-terminal amino acid sequence analysis.

Example 2

Antiserum Preparation

Peptide 1 (CHDMFSQVFDQDDNNQY (SEQ ID NO:6)) was conjugated to bovine serum albumin carrier protein according to standard procedure. This preparation was used to generate three polyclonal antisera in rabbits (EU39, EU40 and EU41; Spring Valley Labs, Woodbine, Md.). The first injection, into the popliteal lymph nodes, of antigen contained 200 μg of antigen emulsified in Freund's Complete Adjuvant. Booster subcutaneous immunizations of 100 μg antigen in Incomplete Freund's Adjuvant were given 14 and 28 days later. Peptide 1 conjugated to keyhole limpet hemocyanin (using standard procedure) was used to generate polyclonal antisera in rabbits (11770, 11771 and 11772; Pocono Rabbit Farm & Laboratory, Inc., Canadensis, Pa.) as described above except that an additional subcutaneous boost was given at 56 days after the initial immunization using 50 μg of Peptide 1 conjugated to BSA as carrier.

Peptide 2 (CDQKEWDDLVSNSPNNDKRPA) conjugated to KLH as carrier was used to generate polyclonal antiserum in rabbit (EU43) at Spring Valley. The first three injections of antigen were as above, with subsequent monthly boosters of 50 μg of antigen on a monthly basis.

Peptide 3 (CDKRPATAADALNDGEVLRL) conjugated to KLH carrier was used to generate three polyclonal antisera in rabbits (11950, 11951 and 11952; Pocono Rabbit Farm & Laboratory, Inc) as described hereinabove.

MAPSpe4-4, MAPSpe4-5 and MAPSpe4-6 are used to generate polyclonal antisera in rabbits (Pocono Rabbit Farm & Laboratory).

The fusion protein product from expression vector pOA5, which comprises amino acids 241–135 of SPE-4, was used to generate two polyclonal antisera in rabbits (EU20, EU21; Spring Valley). pOA5 contains a BamHI/BclI restriction fragment fused in-frame in the pGEX-2T expression vector [Smith and Johnson (1988) *Gene* 67:31–40]. The orientation of the insert was confirmed using dideoxy chain termination sequencing methods and standard techniques. The fusion protein expressed in *E. coli* was purified by affinity chromatography over glutathione-agarose prior to use as an antigen for making antisera. The initial immunization was 100 μg/rabbit with a boost of 100 μg at 14 days followed by boosts at 28 days and monthly intervals thereafter of 50 μg. The same fusion protein was used to generate two polyclonal antisera preparations (9910 and 9911; Pocono Rabbit Farm & Laboratory) using an initial intradermal injection of 200 μg protein in Freund's Complete Adjuvant followed by a boosts of 100 μg antigen at 14 days, 50 μg at 28 and 42 days, with subsequent monthly boosts of 50 μg.

Example 3

Gel Electrophoresis and Immunoblotting

Homogenates are prepared as described above and microcentrifuged at 14,000 rpm for 5 min (1200× G) Membrane pellets (from 100 μg of homogenate protein) are resuspended in 10% sodium dodecyl sulfate (SDS) at room temperature for 30 min, mixed with loading buffer and solubilized proteins are size-separated by SDS polyacrylamide gel electrophoresis (SDS-PAGE, 12% acrylamide) and transferred to Immobilon membranes (Millipore Corporation, Bedford, Mass.) (125 millivolts, 2 hrs). The blots are blocked in 5% nonfat dried milk reconstituted in Tris buffered saline (TBS) at room temperature for 30 min and are then incubated with antisera diluted 1:3000 to 1:5000 in blocking buffer at 4° C. overnight. The antisera raised against the GST-SPE-4 fusion proteins (EU20, EU21, 9910, 9911) are partially purified by preabsorption with GST immobilized on Affigel beads to remove the antibodies reactive with the carrier protein portion of the fusion protein. The antisera raised against the synthetic peptide conjugates (EU39, EU40, EU41, 11770, 11771, 11772) are used without purification. After washing with several changes of TBS, the immunoblots are incubated with horseradish peroxidase-conjugated goat anti-rabbit immunoglobulin G (1:10,000, Bio-Rad Laboratories, Hercules, Calif.) for 60 min. After several washes with TBS, immunoreactive proteins are visualized on the blots using enhanced chemiluminescence as recommended by the manufacturer using Hyperfilm-ECL (ECL, Amersham Corp., Arlington Heights, Ill.) and exposure times of 1 to 120 min. Blots are reprobed with antibodies to the glutamate receptor subunit GluR2/3 to verify the integrity of other membrane proteins and to assess the uniformity of protein loading for the various samples.

Example 4

Human Brain Samples

Postmortem brain samples are collected at autopsy and frozen at −80° C. until use. Samples are homogenized with a Polytron (Source, city, State) at 4° C. in 10 volumes (w/v) of Tris-EDTA buffer (TE; 10 mM Tris-HCl, 1 mM EDTA, pH 7.5), 1 g/ml pepstatin A, 1 μg/ml leupeptin and 1 μg/ml Aprotinin to retard proteolysis. Homogenates are divided into aliquots and frozen at −20° until use.

TABLE 1

Genomic sequence of spe-4 and flanking regions and deduced SPE-4 amino acid sequence [from L'Hernault and Arduengo (1992) supra] (SEQ ID NOS: 1 and 2)

agcttaggatcctagaagaagggttttttcgaaacgaattggagtactgtagagtggttgt -229 tctgaccaagctctgaaagagagcatttctagaaaaaagcacgacatgta<u>caat</u>gcttgt -169

TABLE 1-continued

Genomic sequence of spe-4 and flanking regions and deduced SPE-4
amino acid sequence [from L'Hernault and Arduengo
(1992) supra] (SEQ ID NOS: 1 and 2)

```
tcaattttcacttcaatgttagaaacggcaatattcttccaaaataatattttaaaatg  -109 atttcatcgtgaccccgtgatccaaaccaaagtacaaacatgcacgtgtcatactttgt  -49 ctgccaactcatcaatttcatacaaatctcttgtgctaatattaattttATTACCTGTCT  11

AAAAATGGACACCCTTCGATCGATTTCTAGCGAATTAGTGCGATCTTCACAATTACGATG  71
      M  D  T  L  R  S  I  S  S  E  L  V  R  S  S  Q  L  R  W    19

GACACTGTTCTCTGTTATTGCCAATATGTCACTGACATTGTCTATTTGGATTGGAGTTTA  131
 T  L  F  S  V  I  A  N  M  S  L  T  L  S  I  W  I  G  V  Y    39

CAACATGGAAGTGAATTCTGAATTGAGCAAGACTTATTTTTTGGATCCTTCGTTTGAGCA  191
  N  M  E  V  N  S  E  L  S  K  T  Y  F  L  D  P  S  F  E  Q    59

AACAACTGGAAATTTGCTGTTGGATGGATTTgtgagtttggactgcacattctgagtttt  222
 T  T  G  N  L  L  L  D  G  F                                   69 tgagttagagaataacatttaattcttaatttactagagttatttctgggcatgattcc ccaaatgttttggagcttgattatttcggattgatcctgcaattcaagaaaagagacatc caacattacatttcacaacaagaagttgaatacttttatcattttaaaaaccggcaagaa ataggaagacacgtcttccggtggtctacctacctacttgcctacctatttgtctacgtt tcgcacgaagcataaattgaatttctttgtagtttatcaaaaaagtttgccactcgtaca ttataataatttaatactctcttccactttcagttctcatatttcatttcagATCAATG  229
                                                        I  N    71

GAGTTGGTACAATTCTCGTTCTTGGATGCGTCTCTTTCATAATGCTCGCTTTCGTACTCT  289
 G  V  G  T  I  L  V  L  G  C  V  S  F  I  M  L  A  F  V  L    91

TTGATTTCCGTCGTATCGTAAAAGCCTGGCTCACACTTTCATGTCTTTTGATATTGTTTG  349
 F  D  F  R  R  I  V  K  A  W  L  T  L  S  C  L  L  I  L  F    111

GGGTATCCGCGCAGACTCTTCATGATATGTTTTCACAAGTATTTGACCAAGATGACAACA  409
 G  V  S  A  Q  T  L  H  D  M  F  S  Q  V  F  D  Q  D  D  N    131

ATCAATATTACATGACAATTGTGTTGATAGTGGTTCCAACGGTTGTATATGGGTTCGGAG  469
 N  Q  Y  Y  M  T  I  V  L  I  V  V  P  T  V  V  Y  G  F  G    151

GGATCTATgtaagtgttatgtaaccaaataaaaattaataattatttaagGCATTCTTCT  487
 G  I  Y                                         A  F  F        157

CTAACAGTTCTTTGATTCTTCATCAAATATTCGTTGTCACAAACTGTTCTCTTATCTCCG  547
 S  N  S  S  L  I  L  H  Q  I  F  V  V  T  N  C  S  L  I  S    177

TTTTCTACCTACGAGTTTTTCCAAGCAAAACCACTTGGTTTGTTCTCTGGATTGTTCTAT  607
 V  F  Y  L  R  V  F  P  S  K  T  T  W  F  V  L  W  I  V  L    197

TTTGGGgtttgttttcttcctgtgctcttatgcatttaattaagttttccagATCTCTT  620
 F  W                                                D  L  F    202

TGCCGTTTTAGCACCGATGGGTCCACTCAAAAAAGTTCAAGAAAAGGCTTCAGACTACAG  680
   A  V  L  A  P  M  G  P  L  K  K  V  Q  E  K  A  S  D  Y  S   222

TAAATGCgtaagaatagcaattttcaaaataaatctgattattttcattttcagGTTCTC  693
```

TABLE 1-continued

Genomic sequence of spe-4 and flanking regions and deduced SPE-4 amino acid sequence [from L'Hernault and Arduengo (1992) supra] (SEQ ID NOS: 1 and 2)

```
      K  C                                            V  L    226
AATTTAATTATGTTTTCTGCTAATGAAAAACGTTTAACTGCAGGATCCAATCAAGAAGAG   753
   N  L  I  M  F  S  A  N  E  K  R  L  T  A  G  S  N  Q  E  E  246
ACAAATGAAGGAGAGGAGAGTACAATCAGAAGAACCGTGAAGCAAACGATTGAATATTAT   813
   T  N  E  G  E  E  S  T  I  R  R  T  V  K  Q  T  I  E  Y  Y  266
ACAAAACGTGAAGCTCAAAATGATGAATTTTATCAAAAGATCAGACAACGTCGGGCTGCA   873
   T  K  R  E  A  Q  D  D  E  F  Y  Q  K  I  R  Q  R  R  A  A  286
ATCAATCCAGATTCGGTACCAACTGAGCATAGCCCATTAGgtaagaattaaataaatcat   913
   I  N  P  D  S  V  P  T  E  H  S  P  L                       299
ttagatctttataagaatgacagttgctattattcattttttcttttttcagTAGAAGCCG  922
                                                       V  E  A  302
AGCCATCACCAATCGAATTAAAGGAAAAGAACAGTACCGAGGAGCTCAGTGATGATGAGA   982
   E  P  S  P  I  E  L  K  E  K  N  S  T  E  E  L  S  D  D  E  322
GTGATACATCTGAAACTTCAAGTGGATCATCTAATTTATCGTCTTCCGACTCAAGCACCA  1042
   S  D  T  S  E  T  S  S  G  S  S  N  L  S  S  S  D  S  S  T  342
CTGTGTCAACATCTGATATAAGCACTGCTGAGGAATGTGATCAGAAGGAGTGGGATGATT  1102
   T  V  S  T  S  D  I  S  T  A  E  E  C  D  Q  K  E  W  D  D  362
TGGTCTCTAACAGTCTACCGAACAATGATAAACGGCCAGCCACTGCTGCGGACGCCCTTA  1162
   L  V  S  N  L  P  N  N  D  K  R  P  A  T  A  A  D  A  L     382
ATGATGGAGgtaataatagtttcgtcatattaagcttactctcttaccagcttttttttac  1171
   N  D  G                                                     385
gagaaagtttcagAAGTACTTCGTCTCGGCTTTGGAGATTTCGTCTTCTACAGTCTTCTG  1218
                E  V  L  R  L  G  F  G  D  F  V  F  Y  S  L  L  401
ATTGGTCAAGCGGCTGCCAGCGGATGTCCATTTGCAGTCATTTCTGCCGCTCTTGGTATT  1278
   I  G  Q  A  A  A  S  G  C  P  F  A  V  I  S  A  A  L  G  I  421
TTATTTGGACTTGTTGTGACTCTCACTGTCTTTTCAACTGgtaatcaccatatgaatcac  1318
   L  F  G  L  V  V  T  L  T  V  F  S  T                       434
gaagttcaatactaattgtctcgtttcagAGGAATCCACAAcTcCTGCTcTGCCGTTGCC  1349
                               E  E  S  T  T  P  A  L  P  L  P  445
TGTGATTTGTGGTACTTTCTGCTATTTCAGTTCAATGTTTTCTGGGAGCAACTTTACGG   1409
   V  I  C  G  T  F  C  Y  F  S  S  M  F  F  W  E  Q  L  Y  G  465
ATGAAGCCTCATTTTTCCTGATATTATGTGAACTGATTAAATGTCTTATTTACTTGTCTG  1469
   *
AATGATTAATTTTAAccttttcgtttttttttttcattttatgaatacgaatctatttgg  1484
caaagaatacatagtatcg
```

TABLE 2

Comparison of human S182, mouse S182 and nematode SPE-4 protein
sequences [from Sherrington et. al. (1995) supra]

```
C1                                                            Putative 5' UTR Human                                              N-[*KKEPQEALFSVKQYFYTVAP]

Mouse                                              N-[*EKESQEVLFSLRRYFCPAAP]

SPE-4

VDCCal 1       10      20      30      40      50      60      70

Human   MTELPAPLSYFQNAQMSEDNHLSNTVRSQNDNRERQEHNDRRSLGHPEPLSNGRPQGNSRQVVEQDEEED

Mouse   MTEIPAPLSYFQNAQMSEDSHSSSAIRSQNDSQERQQQHDRQRLONPEPISNGRPQSNSRQVVEQDEEED

SPE-4

VDCCal 71      80      90      100     110     120     130     140

Human   EELTLKYGAKHVIMLFVPVTLCMVVVVATIKSVSFYTRKDGQLIYTPFTEDTETVGQRALHSLLNAAIMI

Mouse   EELTLKYGAKHVIMLFVPVTLCMVVVVATIKSVSFYTRKDGQLIYTPFTEDTETVGQRALHSLLNAAIMI

||*||||*

SPE-4                                                        69 * FINGVGTI

* |* **| * | |

VDCCal                                                      257 - QVVLNSIIKAMVPL

L               R

141   ↓ 150    160   ↓  170     180     190     200     210

Human   SVIVVMTILLVVLYKYRCYKVIHAWLIISSLLLLFFFSFIYLGEVFKTYNVAVDYITVALLIWNEGVVGM

Mouse   SVIVIMTILLVVLYKYRCTKVIHAWLIISSLLLLFFFSFIYLGEVFKTYNVAVDYVTVALLIWNFGVVGM

|*||  |||| |||| |    ||||*** |* **|** |*|  *   *              *||*|

SPE-4   LVLGCVSFIMLAFVLFDFRRIVKAWLTLSCLLILFGVSAQTL  - 118         149 *
        GFGGI

*||   ||||||*          |   *|* *****|* |*|

VDCCal  LHIALLVLFVIIIY284 645SMK--SIASLLLLLFLFIIIF -663

E 211     220     230     240   ↓ 250     260     270       *

Human   ISIHWKGPLRLQQAYLIMISALMALVFIKYLPEWTAWLILAVISVYDLVAVLCPKGPLRMLVETAQERNE

Mouse   IAIHWKGPLRLQQAYLIMISALMALVFIKYLPEWTAWLILAVISVYDLVAVLCPKGPLRMLVETAQERNE

|*|     * * *|||||   *| ||||||||* * *|*|||  ||**|*** * ***|  | * *  |

SPE-4   YAFFSNSSLILHQIFVVTNCSLISVFYLRVFPSKTTWFVLWIVLFWDLFAVLAPMGPLKKVQEKASDYSK

|** ***| |    * *|*|  *| *

VDCCal              1085 * VLSAMMALFTVSTFEGWPALLYKAIDS * 1111

V

281   ↓ 290     300     310     320     330     340     350

Human   TLFPALIYSSTMVWLVNMAEGDPEAQRRVSKNSKYNAESTERESQDTYAENDDGGFSEEWEAQRDSHLGP

Mouse   TLFPALIYSSTMVWLVNMAEGDPEAQRRVPKNPKYNTQRAERETQDSGSGNDDGGFSEEWEAQRDSHLGP

||  ||  |*
```

TABLE 2-continued

Comparison of human S182, mouse S182 and nematode SPE-4 protein
sequences [from Sherrington et. al. (1995) supra]

```
SPE-4       CVLNLIMFS - 232

VDCCa1
                                                                    Y
            351       360       370       380       390       400    *    ↓       420

Human       HRSTPESRAAVQELSSSILAGEDPEERGVKLGLGDFIFYSVLVGKASATASGDWNTTLACFYAILIGLCL Mouse       HRSTPESRAAVQELSGSILTSEDPEERGVKLGLGDFIFYSVLVGXASATASGDWNTTLACFVAILIGLCL

|||*|***|*|* *|*  **    *  ||  |

SPE-4                         388 - LRLGFGDFVFYSLLIGQAAA**SGCPFAVISAALGILFGLVV

VDCCa1

421       430       440       450       460

Human       TLLLLAIFKKALPALPISITFGLVFYFATDYLVQPFMDQLAFHQFYI -C

Mouse       TLLLLAIFKKALPALPISITFGLVFYFATDYLVQPFMDQLAFHQFYI -C

**  ||      ****|  | *  | ** |

SPE-4       TLTVFSTEESTTPALPLPVICGTFCYFSS - 456

VDCCa1
```

Putative amino-acid sequences of the human S182 gene (first line), murine S182
homologue (second line), C. elegans SPE-4 protein (third line), and human α-1D
subunit voltage-dependent Ca²⁺ channel protein (VDCC-α-1D) (fourth line)-identities
indicated by asterisk, similarities by vertical line. Amino acids are numbered from
the first in-phase ATG codon, which was located 21 codons downstream from a TGA stop
codon in the putative 5' UTR (in parentheses) in both species. Transmembrane (TM)
domains (underlined) are bounded by residues 82 to 100 (TM-I); 133 to 154 (TM-II);
164 to 183 (TM-III); 195 to 213 (TM-IV); 221 to 238 (TM-V); 244 to 262 (TM-VI); and
408 to 428 (TM-VII). Two smaller hydrophobic domains are located at residues 282 to
299 and 431 to 456, but are not recognized as putative TM membranes by all algorithms.
The positions of the mutations are indicated by arrows. Potential phosphorylation
sequences exist for MAP kinases (residues 115 and 353) and for protein kinase C
(residues 25, 43, 104, 310, 320, 324, 346, 354 and 397). Putative N-glycoarylation
sequences (indicated by +)exist at Asn 279 and Asn 405. A two-residue shift is made
in the third homologous domain of the SPE-4 amino-acid sequence to maximize homology
(strong similarities are also present without the two residue shift).

The putative human and mouse 5'UTR regions translated into amino acid sequences are given in SEQ ID NO:15 and SEQ ID NO:16, respectively. The deduced amino acid sequences of the human S 182 gene product and the mouse S 182 homolog gene product are given in SEQ ID NO:17 and SEQ ID NO:18, respectively. Partial sequences of the human α-1D subunit voltage dependent Ca²⁺ channel protein (VDCCα1) are given in SEQ ID Nos: 19, 20 and 21. Fragments of the C. elegans SPE-4 protein sequence are given with reference to amino acid numbers; see also SEQ ID NO:2.

TABLE 3

Summary of Immunogens and Antibody Preparations

| Immunogen | Antiserum Name | Rabbit Facility |
|---|---|---|
| Peptide #1 | 11770 | Pocono |
|  | 11771 | Pocono |
|  | 11772 | Pocono |
|  | EU 39 | Spring Valley |
|  | EU 40 | Spring Valley |
|  | EU 41 | Spring Valley |

TABLE 3-continued

Summary of Immunogens and Antibody Preparations

| Immunogen | Antiserum Name | Rabbit Facility |
|---|---|---|
| Peptide #2 | Presently being injected | Spring Valley |
| Peptide #3 | 11950 | Pocono |
|  | 11951 | Pocono |
|  | 11952 | Pocono |
| MAP SPE4-4 | Presently being injected | Pocono |
| MAP SPE4-5 | Presently being injected | Pocono |
| MAP SPE4-6 | not yet injected |  |
| GST Fusion #1 | 9910 | Pocono |
|  | 9911 | Pocono |
|  | EU 20 | Spring Valley |
|  | EU 21 | Spring Valley |

We claim:

1. An immunogenic composition comprising one or more antigenic components, wherein an antigenic component is either an antigenic peptide linked to a carrier molecule to form a peptide-carrier complex or a multiantigenic peptide molecule having a plurality of antigenic peptides of identical amino acid sequence, wherein the antigenic peptide consists of the amino acid sequence selected from the group consisting of CHDMFSQVFDQDDNNQY, SEQ ID NO:6; HDMFSQVFDQDDNNQY, SEQ ID NO:9; CDQKEWDDLVSNSPNNDKRPA, SEQ ID NO:7; DQKEWDDLVSNSPNNDKRPA, SEQ ID NO:10; CDKRPATAADALNDGEVLRL, SEQ ID NO:8; DKRPATAADALNDGEVLRL, SEQ ID NO:11;

CLRLGFGDFVFYSLLIGQA, SEQ ID NO:3,
LRLGFGDFVFYSLLIGQA, SEQ ID NO:12;
CISAALGILFGLVVTLTVFS, SEQ ID NO:13;
ISAALGILFGLVVTLTVFS, SEQ ID NO:4;
CSTTPALPLPVICGTFC, SEQ ID NO:14 and
STTPALPLPVICGTFC, SEQ ID NO:5.

* * * * *

UNITED STATES PATENT AND TRADEMARK OFFICE
CERTIFICATE OF CORRECTION

PATENT NO. : 6,019,974
DATED : February 1, 2000
INVENTOR(S) : L'Hernault

It is certified that error appears in the above-identified patent and that said Letters Patent is hereby corrected as shown below:

Title page, item [56],

In the References:

In the Arduengo et al. reference, after "cell biology," insert --San Francisco, CA--.

In the Arduengo et al. reference, delete "1994.. 5 (Suppl), 1994" and replace with --1994. (Suppl 5)--.

In the Abstract:

In line 9, delete "samples" and replace with --sample--.

In line 10, delete "includes" and replace with --include--.

At column 2, line 22, delete ")" after --NO:2--.

At column 2, line 26, between "PLPVICGTFC" and "." insert (SEQ ID NO:5)--.

At column 3, line 65, delete "call" and replace with --called--.

UNITED STATES PATENT AND TRADEMARK OFFICE
CERTIFICATE OF CORRECTION

PATENT NO. : 6,019,974

DATED : February 1, 2000

INVENTOR: L'Hernault

It is certified that error appears in the above-identified patent and that said Letters Patent is hereby corrected as shown below:

At column 4, line 66, delete the space between "spe-" and "4".

At column 5, line 9, delete "both" and replace with --Both--.

At column 9, line 8, delete "0.1w" and replace with --0.1%--.

At column 9, line 48, delete "241-135" and replace with --241-355--.

At column 9, Table 1, delete "c" at residue 223 and replace with --t--.

At column 10, line 53, delete "Source, city, State)"

At column 11, Table 1, in the second line of the heading, delete "seguence" and replace with --sequence--.

At column 13, Table 1, in the second line of the heading, delete "seguence" and replace with --sequence--.

At column 13, Table 1, delete "A" at residue 832 and replace with --G--.

At column 13, Table 1, delete "c" at residues 1360, 1362 and 1368 and replace with --C--.

At column 13, Table 1, delete "e" at residue 1504 and replace with --a--.

At column 17, line 13 of the legend to Table 2, delete "N-glycoarylation" and replace with --N-glycosylation--.

UNITED STATES PATENT AND TRADEMARK OFFICE
CERTIFICATE OF CORRECTION

PATENT NO. : 6,019,974

DATED : February 1, 2000

INVENTOR : L'Hernault

It is certified that error appears in the above-identified patent and that said Letters Patent is hereby corrected as shown below:

At columns 15, 16, 17 and 18, delete Table 2 and replace with Table 2 below

TABLE 2

Comparison of human S182, mouse S182 and nematode SPE-4 protein sequences [from Sherrington et.al. (1995) supra]

```
                                                            Putative 5'UTR
                                                 N- [*KKEPQEALFSVKQYFYTVAP]
        Human
        Mouse                                    N- [*EKESQEVLFSLRRYFCPAAP]
        SPE-4
        vDCCa1

1        10        20        30        40        50        60        70
        Human   MTELPAPLSYFQNAQMSEDNHLSNTVRSQNDNRERQEHNDRRSLGHPEPLSNGRPQGNSRQVVEQDEEED
        Mouse   MTEIPAPLSYFQNAQMSEDSHSSSAIRSQNDSQERQQQHDRQRLDNPEPISNGRPQSNSRQVVEQDEEED
        SPE-4
        vDCCa1

71       80        90       100       110       120       130       140
        Human   EELTLKYGAKHVIMLFVPVTLCMVVVVATIKSVSFYTRKDGQLIYTPFTEDTETVGQRALHSILNAAIMI
        Mouse   EELTLKYGAKHVIMLFVPVTLCMVVVVATIKSVSFYTRKDGQLIYTPFTEDTETVGQRALHSILNAAIMI
                                                                            ||*|||-|*
        SPE-4                                                         69 - FINGVGTI
                                                                       *|* **| * | |
        vDCCa1                                                       257 - QVVLNSIIKAMVPL
```

UNITED STATES PATENT AND TRADEMARK OFFICE
CERTIFICATE OF CORRECTION

Page 4 of 5

PATENT NO. : 6,019,974
DATED : February 1, 2000
INVENTOR(S) : L'Hernault

It is certified that error appears in the above-identified patent and that said Letters Patent is hereby corrected as shown below:

```
                   L              R
        141    ↓ 150     160   ↓  170       180       190       200       210
Human          SVIVVMTILLVVLYKYRCYKVIHAWLIISSLLLLFFFSFIYLGEVFKTYNVAVDYITVALLIWNFGVVGM
Mouse          SVIVIMTILLVVLYKYRCYKVIHAWLIISSLLLLFFFSFIYLGEVFKTYNVAVDYITVALLIWNFGVVGM
               |•||  ||||  ||||  |    ||||•••  |•  ••|••  |•|   •                  •||•|
SPE-4          LVLGCVSFIMLAFVLFDFRRIVKAWLTLSCLLILFGVSAQTL · 118         149 · GFGGI
               •||   |||||||•          |   •|•  •••••|•  |•|
VDCCα1         LHIALLVLFVIIIY284  645SMK··SIASLLLLLFLFIIIF  ·663

E
        211       220       230       240   ↓  250       260       270        +
Human          ISIHWKGPLRLQQAYLIMISALMALVFIKYLPEWTAWLILAVISVYDLVAVLCPKGPLRMLVETAQERNE
Mouse          IAIHWKGPLRLQQAYLIMISALMALVFIKYLPEWTAWLILAVISVYDLVAVLCPKGPLRMLVETAQERNE
               |•|       • • •|||||   •|  |||||||•  •  •||•|||   ||••|•••  •  •••| |  •  |
SPE-4          YAFFSNSSLILHQIFVVTNCSLISVFYLRVFPSKTTWFVLWIVLFWDLFAVLAPMGPLKKVQEKASDYSK
                              |••  •••|  |     •  •|•|  •|  •
VDCCα1                1085 · VLSAMMALFTVSTFEGWPALLYKAIDS · 1111

V
        281  ↓ 290       300       310       320       330       340       350
Human          TLFPALIYSSTMVWLVNMAEGDPEAQRRVSKNSKYNAESTERESQDTVAENDDGGFSEEWEAQRDSHLGP
Mouse          TLFPALIYSSTMVWLVNMAEGDPEAQRRVPKNPKYNTQRAERETQDSGSGNDDGGFSEEWEAQRDSHLGP
               ||  ||  |•
SPE-4          CVLNLIMFS · 232
VDCCα1
```

UNITED STATES PATENT AND TRADEMARK OFFICE
CERTIFICATE OF CORRECTION

PATENT NO. : 6,019,974
DATED : February 1, 2000
INVENTOR(S) : L'Hernault

It is certified that error appears in the above-identified patent and that said Letters Patent is hereby corrected as shown below:

```
                                                               Y
            351      360      370      380       390      400  -  ↓        420
Human            HRSTPESRAAVQELSSSILAGEDPEERGVKLGLGDFIFYSVLVGKASATASGDWNTTIACFVAILIGLCL
Mouse            HRSTPESRAAVQELSGSILTSEDPEERGVKLGLGDFIFYSVLVGKASATASGDWNTTIACFVAILIGLCL
                   ||**|***|***|*|*  **      *  ||  **|**
SPE-4                      388 - LRLGFGDFVFYSLLIGQAAA- -SGCPFAVISAALGILFGLVV
VDCCα1

421      430      440      450       460
Human            TLLLLAIFKKALPALPISITFGLVFYFATDYLVQPFMDQLAFHQFYI -C
Mouse            TLLLLAIFKKALPALPISITFGLVFYFATDYLVQPFMDQLAFHQFYI -C
                 **  ||       ****|  |  *  |  '**  |
SPE-4            TLTVFSTEESTTPALPLPVICGTFCYFSS - 456
VDCCα1
```

Signed and Sealed this

First Day of May, 2001

NICHOLAS P. GODICI

Attest:

Attesting Officer       Acting Director of the United States Patent and Trademark Office